(12) United States Patent
Furukawa et al.

(10) Patent No.: US 8,389,755 B2
(45) Date of Patent: Mar. 5, 2013

(54) GAS ADSORPTION MATERIAL, PRECURSOR OF SAME, AND METHOD OF PRODUCING GAS ADSORPTION MATERIAL

(75) Inventors: Masahiro Furukawa, Nagoya (JP); Masashi Goto, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 44 days.

(21) Appl. No.: 13/074,353

(22) Filed: Mar. 29, 2011

(65) Prior Publication Data

US 2011/0178320 A1 Jul. 21, 2011

Related U.S. Application Data

(63) Continuation of application No. PCT/JP2009/061760, filed on Jun. 26, 2009.

(30) Foreign Application Priority Data

Sep. 29, 2008 (JP) .................................. 2008-250964

(51) Int. Cl.
*C07F 13/00* (2006.01)
*C07F 1/00* (2006.01)
*C07F 3/00* (2006.01)
*C07F 15/00* (2006.01)

(52) U.S. Cl. .......... 556/49; 556/115; 556/135; 556/147; 556/150; 556/184

(58) Field of Classification Search .................. 556/115, 556/135, 49, 147, 150, 184
See application file for complete search history.

(56) References Cited

FOREIGN PATENT DOCUMENTS

| | | |
|---|---|---|
| JP | 2000-309592 | 11/2000 |
| JP | 2002-128732 | 5/2002 |
| JP | 2004-161675 | 6/2004 |
| JP | 2006-218349 | 8/2006 |
| JP | 2006-220168 | 8/2006 |
| JP | 2006-297278 | 11/2006 |
| JP | 2006-328051 | 12/2006 |
| WO | 2004/037895 A1 | 5/2004 |

OTHER PUBLICATIONS

Wong-Foy, Antek G., et al. "*Exceptional $H_2$ Saturation Uptake in Microporous Metal-Organic Frameworks*," J. Am. Chem. Soc. 2006, 128, pp. 3494-3495.
Mueller, U., et al. "*Metal-organic frameworks-prospective industrial applications*," J. Mater. Chem., 2006, 16, pp. 626-636.
Vitillo, Jenny G., et al. "*Role of Exposed Metal Sites in Hydrogen Storage in MOFs*," J. Am. Chem. Soc. 2008, 130, pp. 8386-8396.
Tranchemontagne, David J., et al. "*Room temperature synthesis of metal-organic frameworks: MOF-5, MOF-74, MOF-177, MOF-199, and IRMOF-0*," Tetrahedron 64 (2008), pp. 8553-8557.
Extended European Search Report dated Jun. 20, 2012.

*Primary Examiner* — Porfirio Nazario Gonzalez
(74) *Attorney, Agent, or Firm* — Burr & Brown (57) ABSTRACT

A gas adsorption material has a three-dimensional structure wherein a ligand (p-hydroxybenzoic acid) having an aromatic ring as a principal skeleton containing, a carboxyl group and a functional group capable of forming a coordinate bond, the functional group being other than the carboxyl group, and a metal nucleus (Zn) are bonded to each other at a ratio of 1:1. The ligand contains a functional hydroxyl group other than the carboxyl group, and the carboxyl group and the functional group other than the carboxyl group are bonded in at least one position to the metal nucleus. The gas adsorption material is produced by drying a precursor obtained by reacting the ligand and the metal nucleus, dissolving the dried precursor in an organic solvent, heating and stirring a resultant solution to form a three-dimensional structure that includes the organic solvent as a crystal solvent, and removing the crystal solvent.

16 Claims, 10 Drawing Sheets

Precursor before drying

Precursor after drying

GAS ADSORPTION MATERIAL, PRECURSOR OF SAME, AND METHOD OF PRODUCING GAS ADSORPTION MATERIAL

TECHNICAL FIELD

The present invention relates to a gas adsorption material, a precursor of the gas adsorption material, and a method of producing the gas adsorption material.

BACKGROUND ART

Hitherto, Metal-Organic Frameworks (MOFs) prepared by three-dimensionally organizing transition metal ions and organic molecules so as to form nano-pores having an ordered size and array have been reported as gas adsorption materials (see, e.g., Non-Patent Documents 1 and 2). Also, a technique of synthesizing one type of MOFs, i.e., $Zn_4O(2,6$-naphthalene dicarboxylate anion$)_3$, in diethylformamide (DEF) and introducing the synthesized MOF to a pressure-tight vessel is proposed (see, e.g., Patent Document 1). Patent Document 1 proposes a method of, after introducing the synthesized MOF to the pressure-tight vessel together with the DEF, replacing the DEF with a solvent (chloroform) which has higher volatility than the DEF and which does not cause phase dissociation with respect to the DEF, and expelling the chloroform from the pressure-tight vessel. With the proposed method, $Zn_4O(2,6$-naphthalene dicarboxylate anion$)_3$ can be filled in the pressure-tight vessel without being exposed to the atmosphere, and the hydrogen-gas adsorption capacity of the MOF can be increased by preventing adsorption of undesired gases (e.g., water vapor) before use. Further, another technique of, after synthesizing the MOF, forming a coating that allows adsorbed gas (e.g., hydrogen) to pass therethrough, but that does not allow undesired gases (e.g., water vapor) to pass therethrough, is proposed to be able to prevent adsorption of the undesired gases (e.g., water vapor) before use and to increase the hydrogen-gas adsorption capacity of the MOF (see, e.g., Patent Document 2).

[Non-Patent Document 1] J. Am. Chem. Soc., 2006, 128, 3494-3495

[Non-Patent Document 2] J. Mater. Chem., 2006, 16, 626-636

[Patent Document 1] Japanese Unexamined Patent Application Publication No. 2006-220168

[Patent Document 2] Japanese Unexamined Patent Application Publication No. 2006-218349

DISCLOSURE OF INVENTION

In the gas adsorption materials proposed in Non-Patent Documents 1 and 2 and Patent Documents 1 and 2, however, because an asymmetrical unit ($[Zn_4O(OOCC_6H_4COO)_3]$) and a unit lattice are relatively large, sizes of formed pores may be relatively large and selectivity of the adsorbed gas may be relatively low in some cases. As another problem, because a ligand has two carboxyl groups which cross-link metal nucleuses, the pore size is increased. Therefore, when pores are brought into a vacuum state, unstable condition may be caused due to application of a large load. Thus, binding between the carboxyl groups and the metal nucleuss are hydrolyzed by the adsorbed water vapor, and the structure of the MOF becomes more apt to collapse.

The present invention has been made in view of the problems described above, and a primary object of the present invention is to provide a novel gas adsorption material that can improve an amount of adsorbed hydrogen, selectivity of hydrogen adsorption, and structural stability, as well as a precursor of the gas adsorption material and a method of producing the gas adsorption material.

As a result of conducting intensive studies with intent to achieve the above-mentioned object, the inventors have found that the amount of adsorbed hydrogen, the selectivity of hydrogen adsorption, and the structural stability can be improved by forming a three-dimensional structure in which a ligand consisting essentially of an aromatic ring as a principal skeleton containing, a carboxyl group and a functional group capable of forming a coordinate bond, the functional group being other than the carboxyl group, and a metal nucleus are bonded to each other at a ratio of 1:1 in a building unit. The present invention has been accomplished on the basis of that finding.

Specifically, the gas adsorption material according to the present invention has a three-dimensional structure in which a ligand consisting essentially of an aromatic ring as a principal skeleton containing, a carboxyl group and a functional group capable of forming a coordinate bond, the functional group being other than the carboxyl group, and a metal nucleus are bonded to each other at a ratio of 1:1 in a building unit.

Further, in a precursor of a gas adsorption material, according to the present invention, a ligand consisting essentially of an aromatic ring as a principal skeleton containing, a carboxyl group and a functional group capable of forming a coordinate bond, the functional group being other than the carboxyl group, and a metal nucleus are bonded to each other at a ratio of 2:1 in a building unit.

Still further, a method of producing a gas adsorption material, according to the present invention, comprises:

a precursor synthesizing step of reacting a ligand consisting essentially of an aromatic ring as a principal skeleton containing, a carboxyl group and a functional group capable of forming a coordinate bond, the functional group being other than the carboxyl group, with a metal nucleus to form a precursor;

a structure constructing step of causing the precursor to be dissolved in an organic solvent and to develop a reaction, thereby constructing a three-dimensional structure in which the ligand and the metal nucleus are bonded to each other with inclusion of the organic solvent; and a porous body forming step of removing the organic solvent from the three-dimensional structure to form a porous body.

The gas adsorption material, the precursor of the gas adsorption material, and the method of producing the gas adsorption material, described above, can improve the amount of adsorbed hydrogen, the selectivity of hydrogen adsorption, and the structural stability. Though not fully clarified, the reason of providing those advantages can be thought of as follows. For example, pores formed through the steps of reacting the carboxyl group and the functional group capable of forming the coordinate bond and being other than the carboxyl group, both of which groups are contained in the ligand, with the metal nucleus, and then removing the organic solvent have sizes that are more suitable to more selectively adsorb hydrogen. Further, a pore structure formed by removing the organic solvent is impregnable and collapse of the pore structure is suppressed even after the gas adsorption material has adsorbed, e.g., water.

Herein, the expression "the ligand and the metal nucleus are bonded to each other at a ratio of 1:1 in a building unit" implies that the intended building unit differs from a building unit in which the ligand and the metal nucleus are bonded to each other at a ratio of 2:1 or a building unit in which the ligand and the metal nucleus are bonded to each other at a ratio of 4:1. In other words, the bonding ratio is not required to be exactly 1:1, and it may be in the range of 0.85:1 to 1.15:1, for example, in consideration of the presence of impurities.

DESCRIPTION OF THE PREFERRED EMBODIMENTS

The gas adsorption material according to the present invention has a three-dimensional structure in which a ligand consisting essentially of an aromatic ring as a principal skeleton containing, a carboxyl group and a functional group capable of forming a coordinate bond, the functional group being other than the carboxyl group, and a metal nucleus are bonded to each other at a ratio of 1:1 in a building unit. When the ratio between the ligand and the metal nucleus is 1:1, the size of a unit lattice or an asymmetrical unit can be reduced, and hence a three-dimensional structure having smaller pores can be formed. The ligand consisting essentially of the aromatic ring as the principal skeleton containing, the carboxyl group and the functional group capable of forming the coordinate bond, the functional group being other than the carboxyl group, may form a three-dimensional structure in which at least one of the carboxyl group and the functional group is bonded to the metal nucleus. Herein, the "aromatic ring as the principal skeleton" is just required to have an aromatic ring as a principal skeleton and may include the case where a carbon chain is linked to the aromatic ring. The principal skeleton of the ligand is preferably an aromatic ring. The aromatic ring may be a monocyclic aromatic ring, such as a benzene ring or a polycyclic aromatic ring, such as a naphthalene ring. Further, each aromatic ring may he a heterocyclic ring. Of the aromatic rings, a smaller ring is more preferable because pores having smaller diameters can be obtained. For that reason, the benzene ring is more preferable. The heterocyclic ring may be at least one or more selected from among pyridine, piperidine, pyrazole, pyrane, and furan. When the principal skeleton is a heterocyclic ring capable of forming a coordinate bond, the functional group can be dispensed with. The functional group being capable of forming the coordinate bond and being other than the carboxyl group can be, for example, a functional group containing an atom that has an unshared electron pair. Examples of an element having an unshared electron pair include oxygen, nitrogen, sulfur, phosphorous, and halogens. The functional group contained in the aromatic ring as the principal skeleton may be at least one or more of a hydroxyl group, an amino group, and a heterocyclic ring. Of those examples, the hydroxyl group is preferable from the viewpoint of enabling a stable bond to be formed. Examples of the amino group include —$NH_2$, —$NHR^1$, —$NR^1R^2$ ($R^1$ and $R^2$ are each an alkyl group having a carbon number of 1 to 3). Examples of the heterocyclic ring are as per mentioned above. If the functional group is the carboxyl group, this is not preferable because the ligand contains two carboxyl groups and the formed three-dimensional structure becomes unstable. From the viewpoint of forming a three-dimensional structure that is electrically neutral, the functional group is more preferably caused to have a negative charge, for example, by desorbing a proton. Moreover, of the above-mentioned examples, the hydroxyl group is more preferable from the viewpoint of that the length of the formed skeleton is suitable. The carboxyl group and the functional group, which is capable of forming a coordinate bond and which is other than the carboxyl group, may be located at any of ortho-positions, meta-positions, and para-positions. From the viewpoint of less steric hindrance when the three-dimensional structure is constructed, the meta-positions are preferable and the para-positions are more preferable. A substitution site of the functional group may be single or plural. The ligand is most preferably hydroxybenzoic acid. In the gas adsorption material according to the present invention, the metal nucleus is preferably one or more selected from among Zn, Cu, Mg, Al, Mn, Fe, Co and Ni from the viewpoint of easiness in obtaining the desired gas adsorption material. Of those elements, Zn, Cu, etc. are more preferable. Further, the metal nucleus may be a metal cluster made of plural metal ions. Examples of the metal cluster include $Zn_4O$, etc.

The structure of the gas adsorption material according to the present invention is not clarified, but it may have a building unit expressed by a composition formula given as the following general formula (1). In the general formula (1), "M" is a metal nucleus, "X" is a functional group which is capable of forming a coordinate bond and which is other than a carboxyl group, "R" is a principal skeleton of a ligand, and "n" is a positive integer. More specifically, M may be one or more metal ions selected from among Zn, Cu, Mg, Al, Mn, Fe, Co and Ni, X may be at least one of a hydroxyl group, an amino group, and a heterocyclic ring, and R may be a carbon chain including an aromatic ring (i.e., an aromatic ring as the principal skeleton). When R is a heterocyclic ring capable of forming a coordinate bond, X may be dispensed with. The rational formula (1) can be determined from a composition formula obtained with an elemental analysis of a dried sample by using an atomic absorption spectrometry or a gas analyzer, for example, and from functional groups identified based on an IR spectrum, for example. Preferably, the three-dimensional structure is formed by polymerization of the building unit, a compound expressed by the following general formula (2). In more detail, the compound expressed by the general formula (2) has the three-dimensional structure formed by the building unit in which a Zn ion ($Zn^{2+}$) as the metal nucleus and a ligand ($^-OC_6H_4COO^-$) are bonded at a ratio of 1:1. While the formulae (1) and (2) are set forth herein, the gas adsorption material is not particularly limited to those formulae. The gas adsorption material is just required to have the three-dimensional structure in which the ligand consisting essentially of the aromatic ring as the principal skeleton containing, the carboxyl group and the functional group capable of forming the coordinate bond, the functional group being other than the carboxyl group, and a metal nucleus are bonded to each other.

[Chemical Formula 1]

$$[M(X-R-COO)]_n \quad \text{Formula (1)}$$

(where M is a metal nucleus, X is a functional group which is capable of forming a coordinate bond and which is other than a carboxyl group, R is an aromatic ring as a principal skeleton, and "n" is a positive integer)

[Chemical Formula 2]

$$[Zn(O-C_6H_4-COO)]_n \quad \text{Formula (2)}$$

(where n is a positive integer)

A method of producing the gas adsorption material according to the present invention will be described below. The method of producing the gas adsorption material according to the present invention may include (1) a precursor synthesizing step of reacting a ligand consisting essentially of an aromatic ring as a principal skeleton containing, a carboxyl group and a functional group capable of forming a coordinate bond, the functional group being other than the carboxyl group, with a metal nucleus to form a precursor, (2) a structure constructing step of causing the precursor to be dissolved in an organic solvent and to develop a reaction, thereby constructing a three-dimensional structure in which the ligand and the metal nucleus are bonded to each other with inclusion of the organic solvent, and (3) a porous body forming step of removing the organic solvent from the three-dimensional structure to form a porous body. Those steps will be described one by one.

(1) Precursor Synthesizing Step

The above-described ligand can be used as a ligand that is one starting material of the precursor. In the ligand, preferably, the functional group being capable of forming the coordinate bond and being other than the carboxyl group is a hydroxyl group, an amino group, or a heterocyclic ring. Further, the principal skeleton is a carbon chain including an aromatic ring, and the carboxyl group and the functional group, which is capable of forming the coordinate bond and which is other than the carboxyl group, are bonded to the principal skeleton. Most preferably, the ligand is hydroxybenzoic acid. A salt of a metal nucleus can be used as the metal nucleus that is another starting material of the precursor. Examples of the salt of the metal nucleus include hydroxides, chlorides, nitrates, and sulfates. Of those examples, hydroxides are preferable because they more easily react with the acidic ligand having the carboxyl group and the hydroxyl group and they hardly produce undesired substances. Of the hydroxides, zinc hydroxide is preferable. The ligand and the metal nucleus are mixed and reacted with each other in a solvent to synthesize the precursor. Examples of the solvent include water, alcohol, and an organic solvent. However, water is preferable in consideration of that a product (precursor) is easily soluble, whereas unreacted materials and by-products are hardly soluble and can be easily separated. Further, the mixing is preferably performed under heating in order to promote the production reaction of the precursor. Heating temperature can be set to, e.g., 50 to 100° C. Next, the precursor is obtained by filtering a resulted reaction solution, as required, to remove undesired substances, and by removing the solvent from an obtained filtrate. Removal of the solvent is preferably performed by, e.g., vacuum concentration under heating. Though not exactly clarified, the obtained precursor has a structure in which the ligand consisting essentially of the aromatic ring as the principal skeleton containing, the carboxyl group and the functional group capable of forming the coordinate bond, the functional group being other than the carboxyl group, and the metal nucleus are bonded to each other at a ratio of 2:1 in a building unit. When the metal nucleus is a Zn ion and the ligand is p-hydroxybenzoic acid, the obtained precursor is thought as having a molecular structure (also called a monomer) of one of compounds expressed by the following formulae (3) and (4), for example, on the basis of not only measurement results of an elemental analysis, an IR spectrum, etc., but also literatures including Spectrochim. Acta. Part A 66(2007)262-272, Angew. Chem. Int. Ed. 2004, 43, 5033•5036, etc. The formula (3) represents a monomer in which four carboxyl groups are bonded to two metal nucleus (2-nucleus) in the syn-syn type, and the formula (4) represents a monomer in which two carboxyl groups are bonded to one metal nucleus (mono-nucleus) in the chelating type. When water is used as the solvent, the obtained precursor contains the solvent as crystal water. Therefore, the obtained precursor is preferably dried at the temperature lower than pyrolysis, e.g., at 120° C. or lower. When the precursor is dried, it is preferable to dry the precursor under depressurization for the purpose of lowering the drying temperature and cutting the drying time.

[Chemical Formula 3]

Formula (3)

[Chemical Formula 4]

Formula (4)

(2) Structure Constructing Step

Next, the obtained precursor is dissolved in an organic solvent to develop a reaction. The organic solvent is not limited to particular one as long as it can dissolve the precursor. Examples of the organic solvent usable here include ketones such as acetone, nitriles such as acetonitrile, alcohols such as methanol, and amides such as dimethylformamide and diethylformamide. Of those examples, acetone is preferably used from the viewpoint of having higher volatility and enabling the next porous body forming step to be more easily performed. More preferably, dry acetone is used in consideration of that the dry acetone is less apt to cause a side reaction, such as hydrolysis. After the dissolution, the reaction gradually progresses under stirring. From the viewpoint of promoting the reaction, the solution is preferably heated. For example, when acetone is used as the organic solvent, the heating is preferably performed at 40 to 50° C. It is inferred that, by activating the precursor as mentioned above, the functional group, which is capable of forming the coordinate bond, which is other than the carboxyl group and which is not yet reacted, is caused to newly form a bond with the metal nucleus, whereby the structure of the precursor is collapsed to construct a three-dimensional structure in which the ligand and the metal nucleus are bonded to each other at 1:1 instead. In other words, the structure is changed from the precursor, which is stable in terms of kinetics, to a three-dimensional structure, which is stable in terms of thermodynamics. As the three-dimensional structure is formed in such a way with the progress of the polymerization reaction, solubility lowers and a crystal precipitates in the organic solvent. On that occasion, organic solvent molecules have to compensate for three-dimensionally generated gaps in order to stably construct the three-dimensional structure. Therefore, the organic solvent molecules are taken, as a crystal solvent, into the crystal body. Thus, the starting materials can be stably held in the organic solvent so as to control the polymerization reaction and to generate the desired reaction by temporarily forming the precursor that is highly soluble.

(3) Porous Body Forming Step

Next, after recovering the crystal body by filtration, for example, the crystal solvent included in the crystal body is removed to form a porous body, thereby obtaining the gas adsorption material. The crystal solvent can be removed by heating, for example. More preferably, the heating is performed in a depressurized state. The heating temperature can be set to, e.g., 50 to 150° C. On that occasion, by selecting the organic solvent having higher volatility for use in the structure constructing step, it is possible to set the heating temperature to a lower level and to suppress collapse and deterioration of the structure, which are caused with being removed the crystal solvent. The obtained crystal holds the network of the three-dimensional structure before and after the removal of the crystal solvent, and maintains a regularly arrayed structure. Further, it is inferred that pores are generated in the crystal structure with the removal of the crystal solvent. The obtained gas adsorption material has the three-dimensional structure in which the ligand and the metal nucleus are bonded to each other at the ratio of 1:1 in the building unit, and the pores have sizes suitable for adsorption of hydrogen. Since the gas adsorption material according to the embodiment, fully described above, has the three-dimensional structure in which fine pores are formed and the ligand and the metal nucleus are bonded to each other at the ratio of 1:1 in the building unit and includes the bond formed by functional group capable of forming the coordinate bond and being other than the carboxyl group, the pore sizes can be avoided from increasing undesirably and hydrolysis can be prevented from generating easily, thus providing the impregnable network. Therefore, even when the gas adsorption material is exposed to the atmosphere and adsorbs water vapor, the three-dimensional structure is hard to collapse and the structural stability can be further increased. In addition, since, in the gas adsorption material according to the embodiment, since the pores have suitable sizes, the amount of adsorbed hydrogen and the selectivity of hydrogen adsorption can be further increased.

It is needless to say that the present invention is in no way limited to the above-described embodiment and the present invention can be practiced in various forms without departing from the technical scope of the present invention.

For example, while the foregoing embodiment has been described as including the precursor synthesizing step, the structure constructing step, and the porous body forming step in the method of producing the gas adsorption material, the gas adsorption material may be synthesized directly from the starting materials by omitting the precursor synthesizing step. As one example, the gas adsorption material may be obtained by causing a ligand consisting essentially of an aromatic ring as a principal skeleton containing, a carboxyl group and a functional group capable of forming a coordinate bond, the functional group being other than the carboxyl group, and a metal nucleus to be mixed in an organic solvent to develop a reaction, thereby producing a three-dimensional structure with inclusion of the organic solvent, and then removing the organic solvent (crystal solvent) to form a porous body. The ligand used here can be prepared as per described above. The metal nucleus is preferably in the form of a salt that is easily soluble in a volatile organic solvent, e.g., acetone. Thus, a carboxylate, such as acetate, is preferably used as the metal nucleus. Regardless of whether the precursor synthesizing step is gone through or not, alkali may be added when the three-dimensional structure is constructed. With the addition of alkali, the functional group in the ligand other than the carboxyl group is activated to more easily react with the metal nucleus, thus enabling the three-dimensional structure to be more easily constructed. Examples of the added alkali include inorganic alkali, such as sodium hydroxide or potassium hydroxide, and organic alkali, such as ammonia, triethylamine, or metalalkoxide. Of those examples, the organic alkali is preferable for the reason that it is less apt to produce a side produce, e.g., water. Such a modified method can also produce the gas adsorption material that is improved in the amount of adsorbed hydrogen, the selectivity of hydrogen adsorption, and structural stability.

EXAMPLES

A practical example of producing the gas adsorption material will be described below as EXAMPLE.

(Precursor Synthesizing Step)

11.050 G (80 mmol) of commercially available p-hydroxybenzoic acid ($HOC_6H_4COOH$) made by Kanto Chemical Co., Inc. was put in 400 ml of water and was stirred. Also, 3.976 g (40 mmol) of commercially available zinc hydroxide ($Zn(OH)_2$) was put in 100 ml of water as a solvent and was stirred. Both solutions were mixed and heated at 50° C. for 20 minutes under stirring. A resultant solution before the mixing was a white suspension liquid because of poor solubility of the p-hydroxybenzoic acid and the zinc hydroxide, which are starting materials. After the stirring and the heating, however, precursor substances produced with reactions were almost dissolved and a transparent solution was obtained. Next, undesired substances were removed by filtration, and vacuum concentration under heating was performed on a filtrate at 60° C. for two hours by using a rotary evaporator to remove the solution, whereby a precipitation was generated. A yield of the precipitation was 17.91 g. The precipitation was dried and a precursor of the gas adsorption material was obtained. Various measurements were conducted on samples from the p-hydroxybenzoic acid as the starting material up to the precursor after the drying to study changes thereof.

(Thermogravimetry and Differential Thermogravimetric Analysis (TG-DTA) of Precursor)

Figure 1:
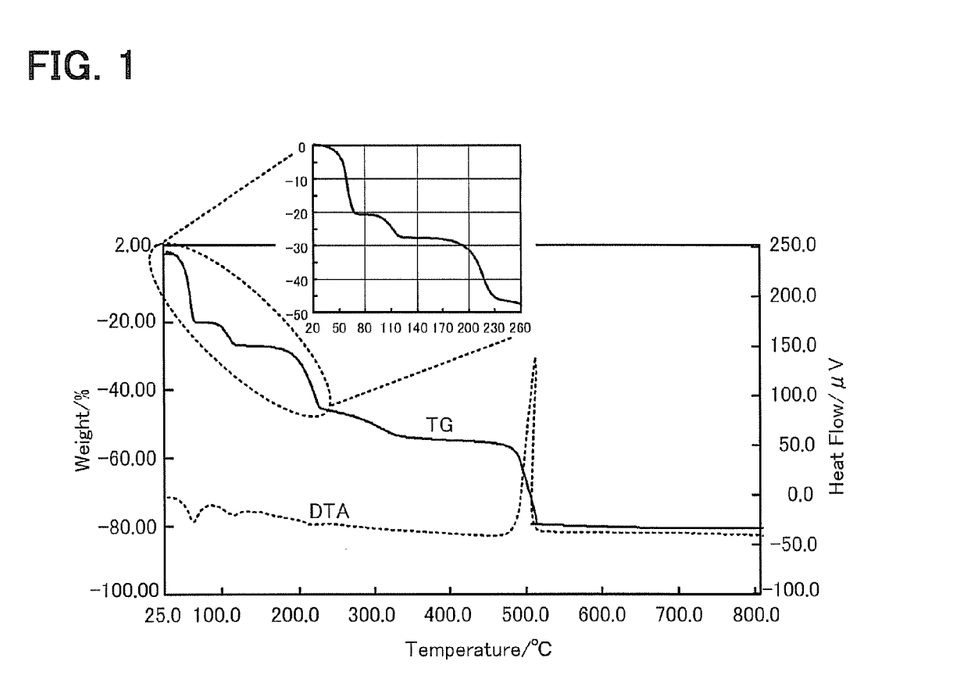
FIG. 1 plots TG-DTA measurement results of a precursor before drying.

FIG. 1 plots results of TG-DTA measurements preformed on the precursor before the drying. As plotted in FIG. 1, a weight reduction and an endothermic peak appeared in three stages over the range of 25° C. to 260° C. Further, a weight reduction and an exothermic peak probably attributable to burning of organic substances appeared near 500° C. With the plotted measurement results, the weight reduction occurred at a rate of by weight until 70° C., 27% by weight until 130° C., and 47% by weight until 260° C. Further, DTA endothermic peaks were observed at 66° C., 118° C. and 214° C. More specifically, the weight reduction until 70° C. was presumably due to desorption of water freely existing in crystal lattices (i.e., crystal water) and the weight reduction until 130° C. was presumably due to desorption of water bound to an Zn ion in the precursor (i.e., coordinated water). On the other hand, the weight reduction until 260° C. was presumably due to decomposition of the precursor. In view of the above point, the drying condition of the precursor was set to 120° C. under depressurization, and the weight reduction was measured under such a condition. As a result, a reduction of 30% by weight was measured. Assuming the precursor to be a monomer $[Zn_2(HOC_6H_4COO)_4]$ expressed by the formula (3), the amount of such a weight reduction was equivalent to water in 16 molecules per monomer and was substantially matched with the value (27.3% by weight) of the weight reduction until 130° C., which was obtained with the TG-DTA measurements.

(Identification of Unit Structure of Precursor)

Figure 2:
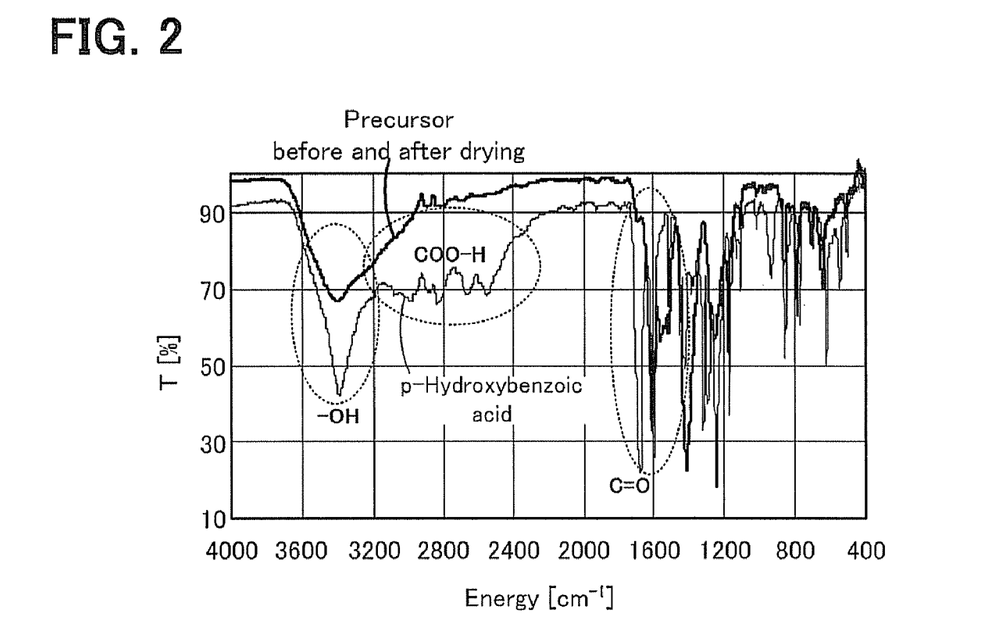
FIG. 2 plots measurement results of IR spectra of p-hydroxybenzoic acid and the precursor after the drying, FIG. 3 plots measurement results of powder X-ray diffraction patterns of the p-hydroxybenzoic acid and the precursor before and after the drying.
Figure 3:
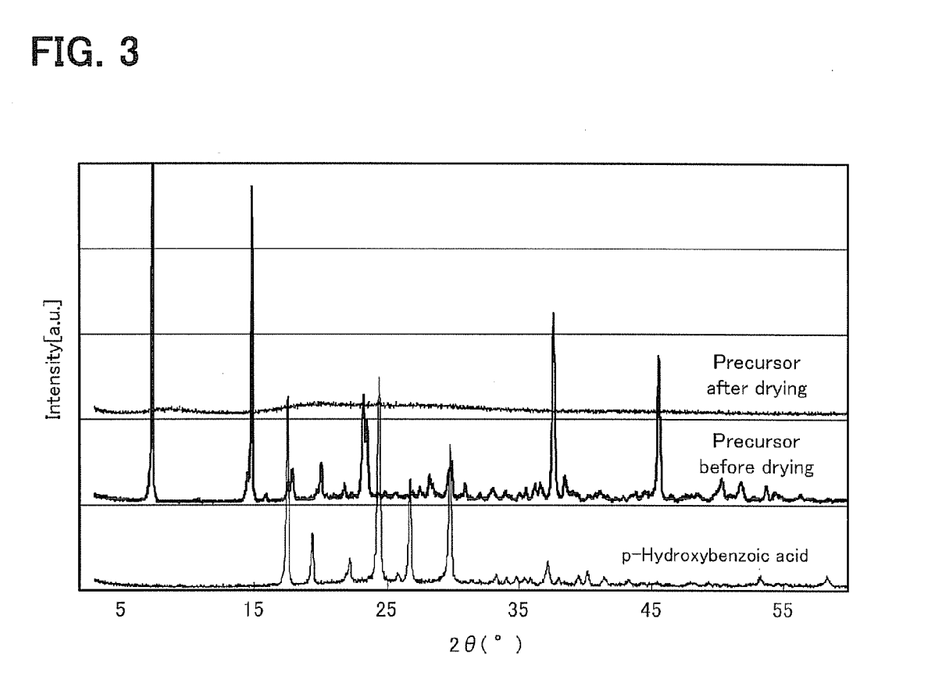

IR spectrum measurements were performed on the p-hydroxybenzoic acid and the precursor after the drying, and an elemental analysis was performed on the precursor after the drying. Further, powder X-ray diffraction patterns were measured on the p-hydroxybenzoic acid and the precursor before and after the drying. IR spectra were measured based on the KBr method by using an IR measuring apparatus (Perkin Elmer Spectrum 2000 made by Perkin Elmer, Inc.). The elemental analysis was performed for C, H and N by using a CHN Coder (MT-5 made by Yanato). For Zn, the elemental analysis was performed by chelate titration using an EDTA solution. Obtained results are given in FIG. 2 and Table 1. Because spectra derived from a hydroxyl (OH) group in a benzene ring and CO were analogous to those of the p-hydroxybenzoic acid as the starting material, as plotted in FIG. 2, the precursor after the drying was inferred to have a structure including the p-hydroxybenzoic acid. Also, because absorptions by O—H in the carboxyl group (COOH) near 2400 to 3200 $cm^{-1}$ were disappeared, the carboxyl group was inferably deprotonated and bonded to Zn. Further, because an absorption by O—H in the hydroxyl group near 3400 $cm^{-1}$ did not change, the hydroxyl group was inferably not changed in particular. Moreover, as listed in Table 1, the obtained precursor showed values close to results calculated for $[Zn_2(HOC_6H_4COO)_4].0.5H_2O$ or $[Zn(HOC_6H_4COO)_2].0.25H_2O$. From those results, the precursor after the drying was inferred to have, for example, the monomer structures expressed by the foregoing formulae (3) and (4). In addition, it was found that the crystal water in 16 molecules, included before the drying, was almost removed through the drying.

TABLE 1

| Precursor | C Weight % | H Weight % | N Weight % | Zn Weight % |
|---|---|---|---|---|
| Measurement Value | 48.99 | 3.11 | 0.00 | 18.73 |
| $[Zn_2(HOC_6H_4COO)_4]$ (Calculated value) | 49.51 | 2.97 | 0.00 | 19.25 |
| $[Zn_2(HOC_6H_4COO)_4]\cdot 0.5H_2O$ (Calculated value) | 48.86 | 3.08 | 0.00 | 19.00 |

(Identification of Organized Structure of Precursor)

Powder X-ray diffraction patterns were measured on the p-hydroxybenzoic acid and the precursor after the drying by using a qualitative X-ray diffraction apparatus (RAD-1B made by Rigaku Corporation). Measurement results are plotted in FIG. 3. As plotted in FIG. 3, the precursor before the drying exhibited the powder X-ray diffraction pattern differing from that of the p-hydroxybenzoic acid. It was therefore inferred, although a detailed crystal structure (organized structure) was not clarified, that the precursor before the drying had a structure differing from that of the starting material from the crystallographic point of view due to bonding with Zn. Also, it was clarified that, by drying the precursor to remove the crystal water, the structure of the precursor was changed to be amorphous from the crystallographic point of view. As discussed above, however, from the results of the IR spectrum measurement and the elemental analysis, the precursor inferably had the monomer structure even after the drying. Stated another way, it was found that, before the drying, precursor monomers formed a network supported by crystal water and the precursor had a regularly arrayed structure, and that the array (organized structure) of the precursor was shifted with removal of the crystal water through the drying, while the monomer structure of the precursor was maintained.

(SEM Observation of Precursor)

Figure 4:
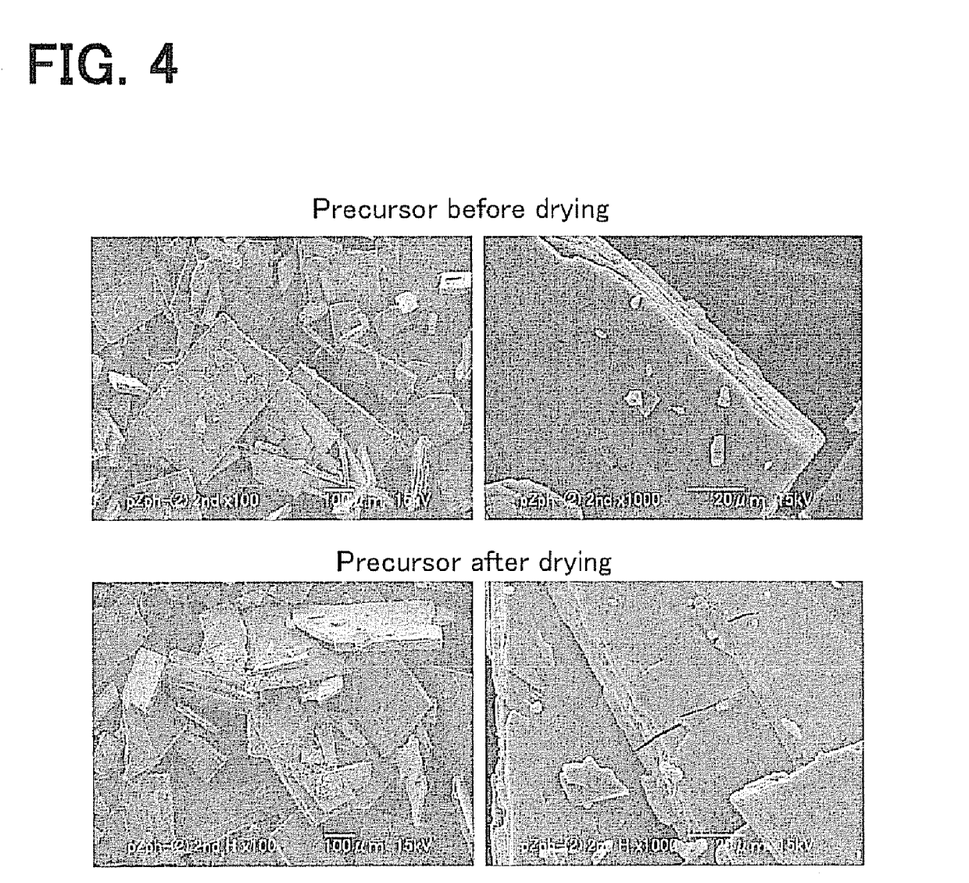
FIG. 4 represents SEM photos of the precursor before and after the drying, FIG. 5 plots TG-DTA measurement results of an acetone-containing product.

SEM observation was performed on the precursor before and after the drying. A scanning electron microscope (JSM-5410 made by JEOL Ltd.) was used in the SEM observation. FIG. 4 represents SEM photos of the precursor before and after the drying. As seen from FIG. 4, while great changes were not found in crystal shape and grain size between before and after the drying, cracks appeared in the surface after the drying. Hence, crystal lattices were inferably contracted (moved) due to the removal of the crystal water.

(Structure Constructing Step and Porous Body Forming Step)

Next, 1.038 g of the precursor obtained after the drying was dissolved in 60 ml of dry acetone that was dried by using anhydrous magnesium sulfate, and a solution was heated and stirred at 50° C. for one hour. In that process, the precursor was first completely dissolved and then gradually precipitated about after the lapse of 30 minutes during the heating. A precipitation produced after the heating and the stirring was separated by filtration, and a product containing acetone (hereinafter referred to as an "acetone-containing product") was obtained. A yield of the acetone-containing product was 0.666 g. Next, the acetone-containing product was dried under depressurization at 120° C. for two hours to remove the contained acetone, whereby a gas adsorption material of EXAMPLE 1, free from acetone, was obtained. A weight reduction caused by removing the acetone was 15% by weight. Various measurements were conducted on samples from the precursor after the drying up to the gas adsorption material of EXAMPLE 1 to study changes thereof.

(Thermogravimetry and Differential Thermogravimetric Analysis (TG-DTA) of Acetone-Containing Product)

Figure 5:
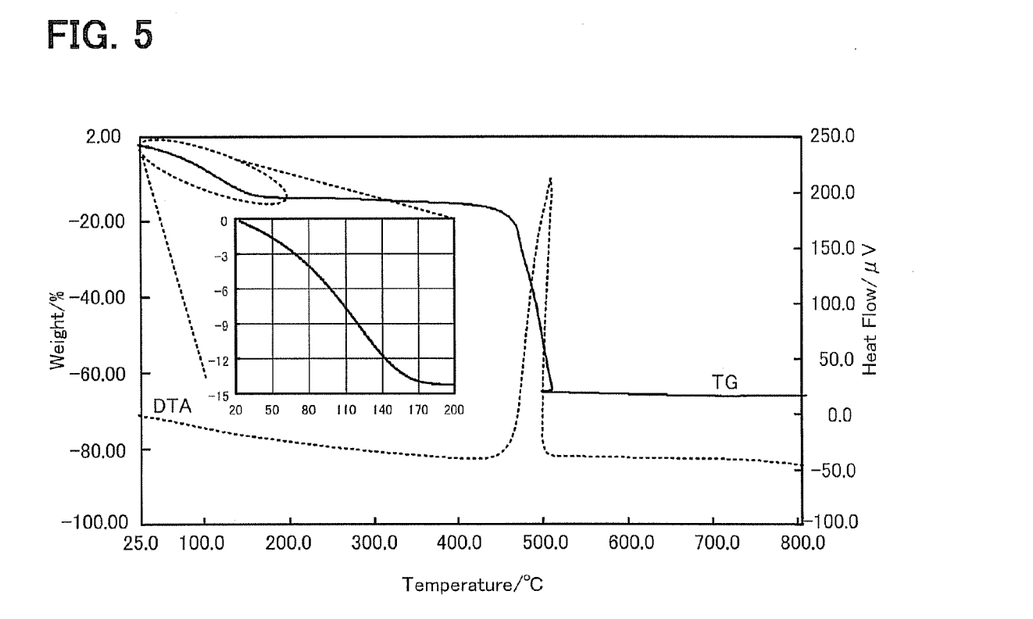

FIG. 5 plots results of TG-DTA measurements performed on the acetone-containing product. As plotted in FIG. 5, a gentle weight reduction appeared until 200° C. Further, a weight reduction and an exothermic peak probably attributable to burning of organic substances appeared near 500° C. In consideration of the boiling point (56° C.) of acetone and decomposition of the structure, along with the above-mentioned results, the condition for removing the acetone in the acetone-containing product was set to 120° C. under depressurization. In this respect, the TG-DTA measurement results exhibited a weight reduction of 14.3% by weight until 200° C. Such a measured value was almost matched with 15% by weight that was measured when the acetone-containing product was dried under depressurization at 120° C. for two hours.

(SEM Observation of Acetone-Containing Product)

Figure 6:
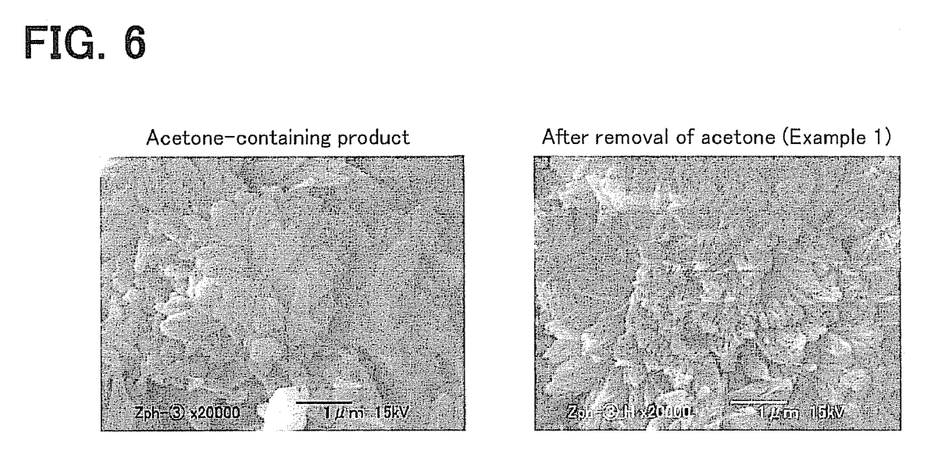
FIG. 6 represents SEM photos of the product before and after removal of acetone, FIG. 7 plots measurement results of IR spectra of the precursor and the product before and after removal of acetone, FIG. 8 plots measurement results of powder X-ray diffraction patterns of the precursor and the product before and after removal of acetone.

SEM observation was performed on the product before and after the removal of the acetone in a similar manner to that in the above-described case of the precursor. FIG. 6 represents SEM photos of the precursor before and after the removal of the acetone. As seen from FIG. 6, great changes were not found in crystal shape and grain size between before and after the removal of the acetone.

(Identification of Unit Structure of Gas Adsorption Material)

Figure 7:
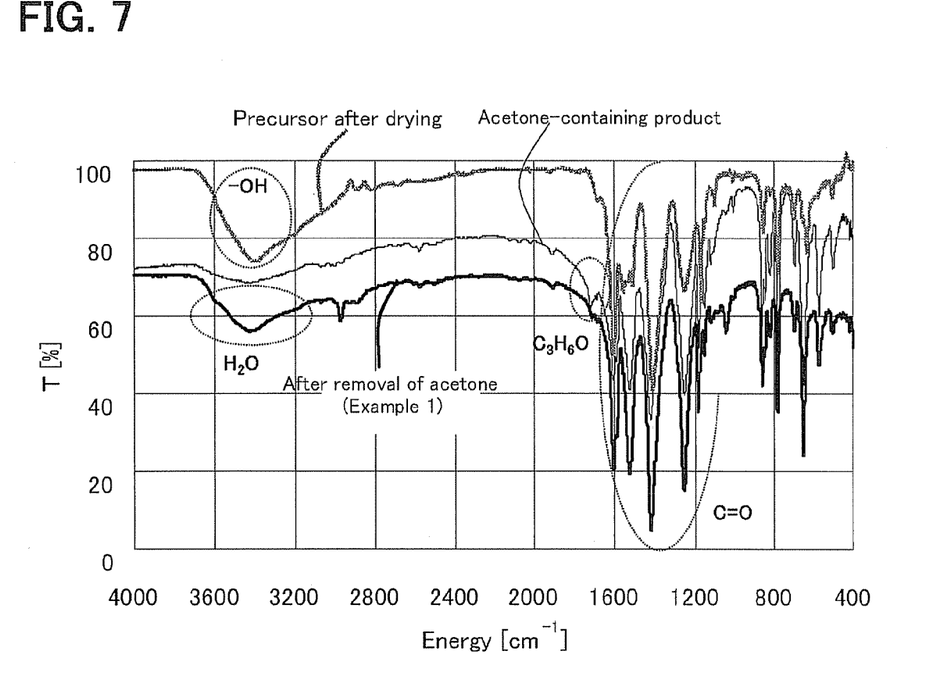

IR spectrum measurements on the product before and after the removal of the acetone and an elemental analysis after the removal of the acetone were performed in a similar manner to that in the above-described case of the precursor. Obtained results are given in FIG. 7 and Table 2. As plotted in FIG. 7, the acetone-containing product exhibited absorption attributable to the acetone near 1700 $cm^{-1}$. Further, in the spectrum of the acetone-containing product, the absorption by O—H in the hydroxyl group near 3400 $cm^{-1}$, which appeared in the measurement of the precursor, was almost disappeared. Therefore, the hydroxyl group was inferably deprotonated and bonded to Zn. Moreover, it was confirmed that because absorption peaks of C=O appearing in the range of 1200 to 1600 $cm^{-1}$ were different from those in the case of the precursor, the bonded state of the carboxyl group and Zn was also different from that in the precursor. Hence, the acetone-containing product was inferably changed to a structure greatly differing from the structure of the precursor. In addition, because, after the removal of the acetone, the absorption attributable to the acetone disappeared and a broad absorption peak specific to O—H in water appeared near 3400 $cm^{-1}$, water in the atmosphere was inferably adsorbed after the removal of the acetone. Still further, as listed in Table 2, the product obtained after the removal of the acetone showed a value close to a result calculated for [Zn(OC$_6$H$_4$COO)]·0.5H$_2$O. Thus, the product obtained after the removal of the acetone inferably had a building unit in which p-hydroxybenzoic acid ($^-$OC$_6$H$_4$COO$^-$) containing the carboxyl group and the hydroxyl group both deprotonated and a Zn ion (Zn$^{2+}$) were bonded at a ratio of 1:1, and the carboxyl group and the hydroxyl group were each bonded in at least one position to the Zn ion. Hence, the gas adsorption material of EXAMPLE 1 inferably had a three-dimensional structure having a repeated unit expressed by the foregoing formula (2), for example, though the type of bonding between the Zn ion and the respective functional groups were not clarified.

TABLE 2

| Gas adsorption material | C Weight % | H Weight % | N Weight % | Zn Weight % |
|---|---|---|---|---|
| Measurement value | 41.08 | 2.01 | 0.00 | 31.44 |
| [Zn(OC$_6$H$_4$COO)]·0.5H$_2$O (Calculated value) | 40.81 | 2.20 | 0.00 | 31.74 |

(Identification of Three-Dimensional Structure of Gas Adsorption Material)

Figure 8:
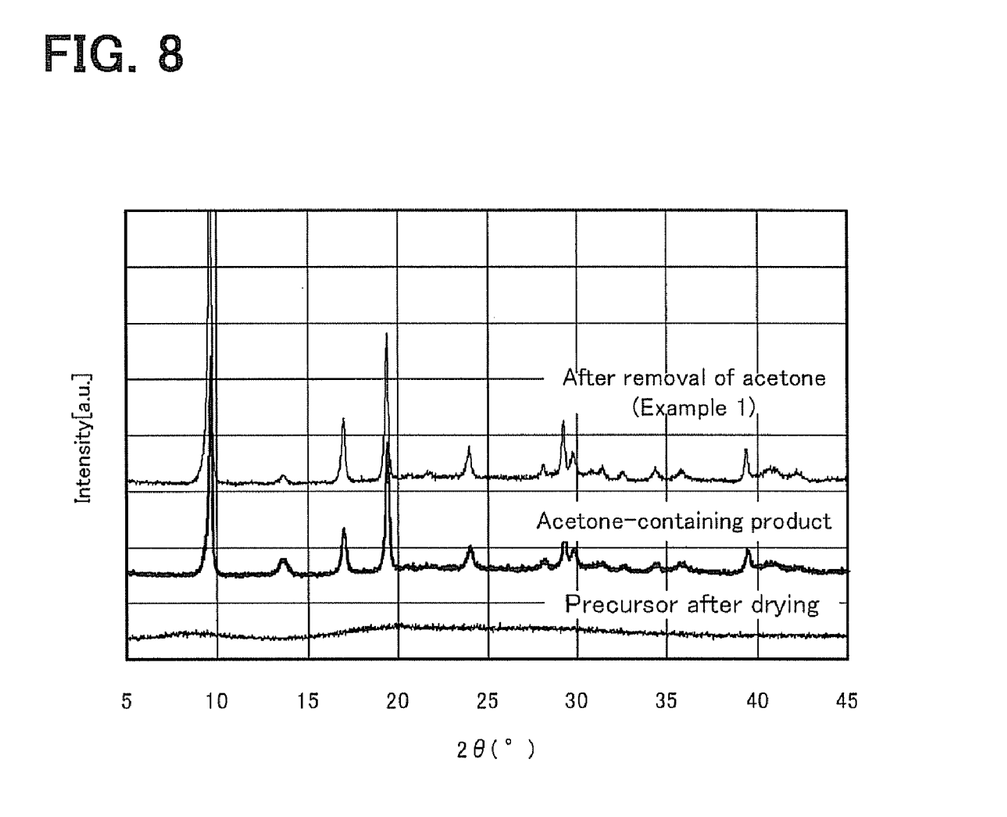

Powder X-ray diffraction patterns were measured on the product before and after the removal of the acetone in a similar manner to that in the above-described case of the precursor. Measurement results are plotted in FIG. 8. It was confirmed that because the acetone-containing product exhibited the diffraction pattern as plotted in FIG. 8, the acetone-containing product had a certain ordered crystal structure though the detailed structure was not clarified. It was also confirmed that because the positions of diffraction peaks did not change even after the removal of the acetone, the structure was not changed with the removal of the acetone. In other words, it was clarified that, unlike the case where the precursor was an organized body of monomers and the organized structure was collapsed upon the crystal water being lost, the obtained gas adsorption material had an impregnable three-dimensional structure which was not collapsed with the removal of the acetone. Further, as a result of leaving the gas adsorption material of EXAMPLE 1 to stand indoors for several days to absorb moisture and then measuring a powder X-ray diffraction pattern thereof, the gas adsorption material of EXAMPLE 1 did not exhibit changes in diffraction peaks. Thus, it was confirmed that the gas adsorption material of EXAMPLE 1 had an impregnable three-dimensional skeleton structure endurable against hydrolysis caused by water vapor, etc.

Comparative Example 1

[Zn$_4$O(OOCC$_6$H$_4$COO)$_3$]$_n$ (Isoreticular metal-organic framework-1: IRMOF-1), which was one type of a zinc complex including terephthalic acid as a cross-linking ligand, was selected as COMPARATIVE EXAMPLE. COMPARATIVE EXAMPLE 1 was formed in accordance with the production method described in Non-Patent Documents 1 and 2. More specifically, respective predetermined amounts of commercially available zinc nitrate hexahydrate, terephthalic acid, and diethylformamide (DEF) were put in a lidded vessel made of polytetrafluoroethylene, and the lidded vessel was placed in a stainless-made heat resistant container that was endurable against 50 atm. The heat resistant container was loaded in an oven and solvothermal synthesis was performed at 130° C. for 20 hours. When the lidded vessel was opened after cooling, a precipitation deposit in the form of brown fine crystal powder was found. The powder was separated by suction filtration, washed three times with DEF, and dried in the atmosphere. Thereafter, the powder was treated at 150° C. under vacuum for 14 hours, whereby fine crystal powder of IRMOF-1 was finally obtained.

Figure 9:
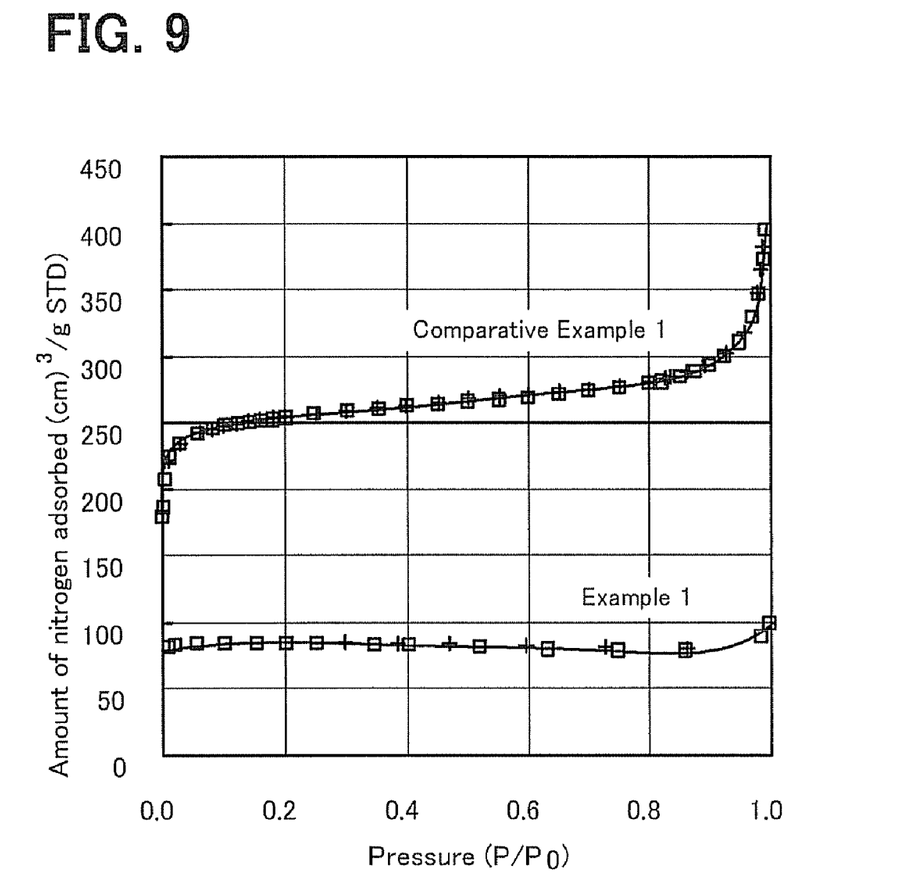
FIG. 9 represents an adsorption isotherm of nitrogen gas at 77K.
Figure 10:
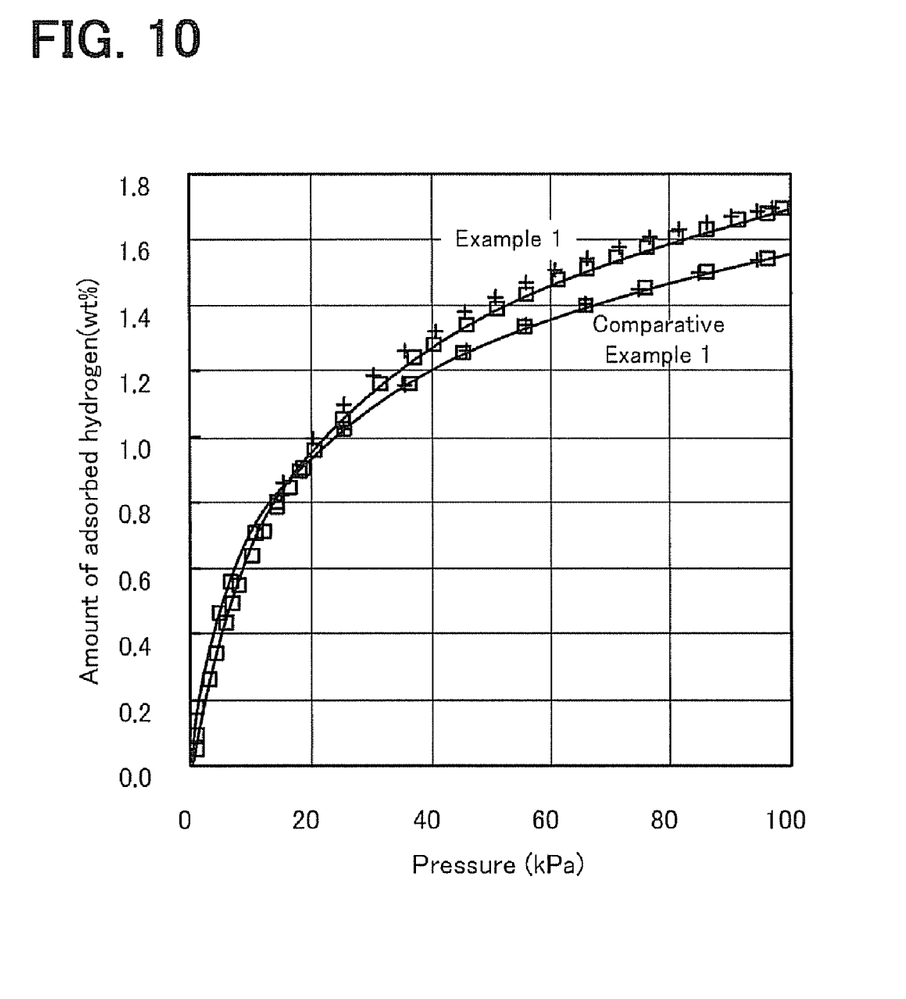
FIG. 10 represents an adsorption isotherm of hydrogen gas at 77K.

Adsorption isotherm measurements of nitrogen gas and hydrogen gas at 77K were performed on the gas adsorption materials of EXAMPLE 1 and COMPARATIVE EXAMPLE 1 by using a specific surface/pore distribution measuring apparatus ASAP2020 (made by Micromeritics Instrument Corporation). FIG. 9 represents an adsorption isotherm of nitrogen gas at 77K, and FIG. 10 represents an adsorption isotherm of hydrogen gas at 77K. As seen from the plotted results, the amount of nitrogen adsorbed by EXAMPLE 1 was about 80 cm$^3$ STD/g lower than that (about 300 cm$^3$ STD/g) adsorbed by COMPARATIVE EXAMPLE 1. On the other hand, the amount of adsorbed hydrogen was a fairly high value, i.e., 1.7 by weight, at 100 kPa, which value was comparable to that obtained with IRMOF-1 (COMPARATIVE EXAMPLE 1), i.e., a typical porous metal complex. A volume-converted value of the above amount of adsorbed hydrogen was 190 cm$^3$ STD/g. Thus, hydrogen was adsorbed twice or more the amount of adsorbed nitrogen (80 cm$^3$ STD/g). Those results were inferably attributable to that pores formed in EXAMPLE 1 had sizes smaller than the molecular diameter (3.64 Å) of nitrogen, but larger than the molecular diameter (2.89 Å) of hydrogen. Also, it was confirmed that when COMPARATIVE EXAMPLE 1 was exposed to the atmosphere, the X-ray diffraction peaks were disappeared and the three-dimensional structure was collapsed in several minutes, whereas EXAMPLE 1 did not exhibit considerable changes in the three-dimensional structure even after absorbing moisture and maintained the skeleton stable against water vapor. Such an adsorption characteristic of EXAMPLE 1 was inferably attributable to that EXAMPLE 1 was adapted for adsorbing hydrogen because of having the three-dimensional structure in which the ligand and the metal nucleus were bonded to each other at the ratio of 1:1 in the building unit, and having the unit lattice or the asymmetric unit so small as to provide fine pores, and that EXAMPLE 1 was avoided from undesirably increasing pore sizes and from being easily hydrolyzed because of having the bond formed by the hydroxyl group, i.e., the functional group other than the carboxyl group. As a result of providing the above-described properties, the gas adsorption material superior in the amount of adsorbed hydrogen, the selectivity of hydrogen adsorption, and the structural stability can be obtained.

This application claims priority on the basis of Japanese Patent Application No. 2008-250964 filed on Sep. 29, 2008, which is hereby incorporated by citation herein in its entirety.

INDUSTRIAL APPLICABILITY

The present invention is applicable to the technical field of gas adsorption materials.

The invention claimed is:

1. A gas adsorption material having a three-dimensional structure in which a ligand consisting essentially of an aromatic ring as a principal skeleton containing, a carboxyl group and a functional group capable of forming a coordinate bond, the functional group being other than the carboxyl group, and a metal nucleus are bonded to each other at a ratio of 1:1 in a building unit.

2. The gas adsorption material according to claim 1, wherein the functional group is one or more of a hydroxyl group, an amino group, and a heterocyclic ring.

3. The gas adsorption material according to claim 1, wherein the metal nucleus is one or more of Zn, Cu, Mg, Al, Mn, Fe, Co and Ni.

4. The gas adsorption material according to claim 1, wherein the building unit has a composition formula expressed by a general formula (1) given below:

[Chemical Formula 1]

$$[M(X-R-COO)]_n \qquad \text{Formula (1)}$$

(where M is a metal nucleus, X is a functional group which is capable of forming a coordinate bond and which is other than a carboxyl group, R is an aromatic ring as a principal skeleton, and "n" is a positive integer).

5. The gas adsorption material according to claim 4, wherein the building unit has a composition formula expressed by a general formula (2) given below:

[Chemical Formula 2]

$$[Zn(O-C_6H_4-COO)]_n \qquad \text{Formula (2)}$$

(where n is a positive integer).

6. A method of producing a gas adsorption material, the method comprising:
   a precursor synthesizing step of reacting a ligand consisting essentially of an aromatic ring as a principal skeleton containing, a carboxyl group and a functional group capable of forming a coordinate bond, the functional group being other than the carboxyl group, with a metal nucleus to form a precursor;
   a structure constructing step of causing the precursor to be dissolved in an organic solvent and to develop a reaction, thereby constructing a three-dimensional structure in which the ligand and the metal nucleus are bonded to each other at a ratio of 1:1 with inclusion of the organic solvent; and
   a porous body forming step of removing the organic solvent from the three-dimensional structure to form a porous body.

7. The method of producing the gas adsorption material according to claim 6, wherein, in the structure constructing step, at least one of acetone, acetonitrile and methanol is used as the organic solvent.

8. The method of producing the gas adsorption material according to claim 6, wherein, in the ligand used in the precursor synthesizing step, the functional group is one or more of a hydroxyl group, an amino group, and a heterocyclic ring.

9. The method of producing the gas adsorption material according to claim 6, wherein, in the precursor synthesizing step, an ion of one or more of Zn, Cu, Mg, Al, Mn, Fe, Co and Ni is used as the metal nucleus.

10. The gas adsorption material according to claim 2, wherein the metal nucleus is one or more of Zn, Cu, Mg, Al, Mn, Fe, Co and Ni.

11. The gas adsorption material according to claim 2, wherein the building unit has a composition formula expressed by a general formula (1) given below:

[Chemical Formula 1]

$$[M(X-R-COO)]_n \qquad \text{Formula (1)}$$

(where M is a metal nucleus, X is a functional group which is capable of forming a coordinate bond and which is other than a carboxyl group, R is an aromatic ring as a principal skeleton, and "n" is a positive integer).

12. The gas adsorption material according to claim 3, wherein the building unit has a composition formula expressed by a general formula (1) given below:

[Chemical Formula 1]

$$[M(X-R-COO)]_n \qquad \text{Formula (1)}$$

(where M is a metal nucleus, X is a functional group which is capable of forming a coordinate bond and which is other than a carboxyl group, R is an aromatic ring as a principal skeleton, and "n" is a positive integer).

13. The method of producing the gas adsorption material according to claim 7, wherein, in the ligand used in the precursor synthesizing step, the functional group is one or more of a hydroxyl group, an amino group, and a heterocyclic ring.

14. The method of producing the gas adsorption material according to claim 7, wherein, in the precursor synthesizing step, an ion of one or more of Zn, Cu, Mg, Al, Mn, Fe, Co and Ni is used as the metal nucleus.

15. The method of producing the gas adsorption material according to claim 8, wherein, in the precursor synthesizing step, an ion of one or more of Zn, Cu, Mg, Al, Mn, Fe, Co and Ni is used as the metal nucleus.

16. The method of producing the gas adsorption material according to claim 6, wherein in the precursor synthesizing step, a precursor is formed in which a ligand consisting essentially of an aromatic ring as a principal skeleton containing a carboxyl group and a functional group, other than the carboxyl group, capable of forming a coordinate bond, and a metal nucleus are bonded to each other at a ratio of 2:1 in a building unit.

* * * * *